United States Patent

Watanabe et al.

[11] Patent Number: 5,913,825
[45] Date of Patent: Jun. 22, 1999

[54] ULTRASONIC PROBE AND ULTRASONIC SURVEY INSTRUMENT

[75] Inventors: Hiroki Watanabe, 3-30-20 Hieidaira, Otsu, Shiga; Mikio Suzuki, Chiba, both of Japan

[73] Assignees: Kanda Tsushin Kogyo Co., Ltd., Tokyo; Hiroki Watanabe, Shiga, both of Japan

[21] Appl. No.: 08/880,974

[22] Filed: Jun. 23, 1997

[30] Foreign Application Priority Data

Jul. 19, 1996 [JP] Japan .................................. 8-208917

[51] Int. Cl.$^6$ .................................................. A61B 08/00
[52] U.S. Cl. ............................................................ 600/459
[58] Field of Search ............................. 73/624; 600/459, 600/442, 437

[56] References Cited

U.S. PATENT DOCUMENTS

| | | | |
|---|---|---|---|
| 4,669,482 | 6/1987 | Ophir | 73/624 |
| 4,901,729 | 2/1990 | Saitoh et al. | 600/459 |
| 5,042,492 | 8/1991 | Dubut | 600/459 |
| 5,394,877 | 3/1995 | Orr et al. | 600/459 |
| 5,619,999 | 4/1997 | Von Behren et al. | 600/459 |

*Primary Examiner*—Marvin M. Lateef
*Assistant Examiner*—Maulin Patel
*Attorney, Agent, or Firm*—Majestic, Parsons, Siebert & Hsue P.C.

[57] ABSTRACT

An ultrasonic scanning instrument uses a probe formed by arranging a plurality of oscillator pieces aligned on a flexible base plate. The oscillator pieces each transmit ultrasonic waves into a target body and receive reflected waves. Sensors are attached to the flexible base plate to detect degrees of flexure of the base plate. The flexible base plate becomes curved according to the curved contact surface of the target body and its degree of flexure measured by the sensors is incorporated into a sectional view displayed on a display device.

11 Claims, 4 Drawing Sheets

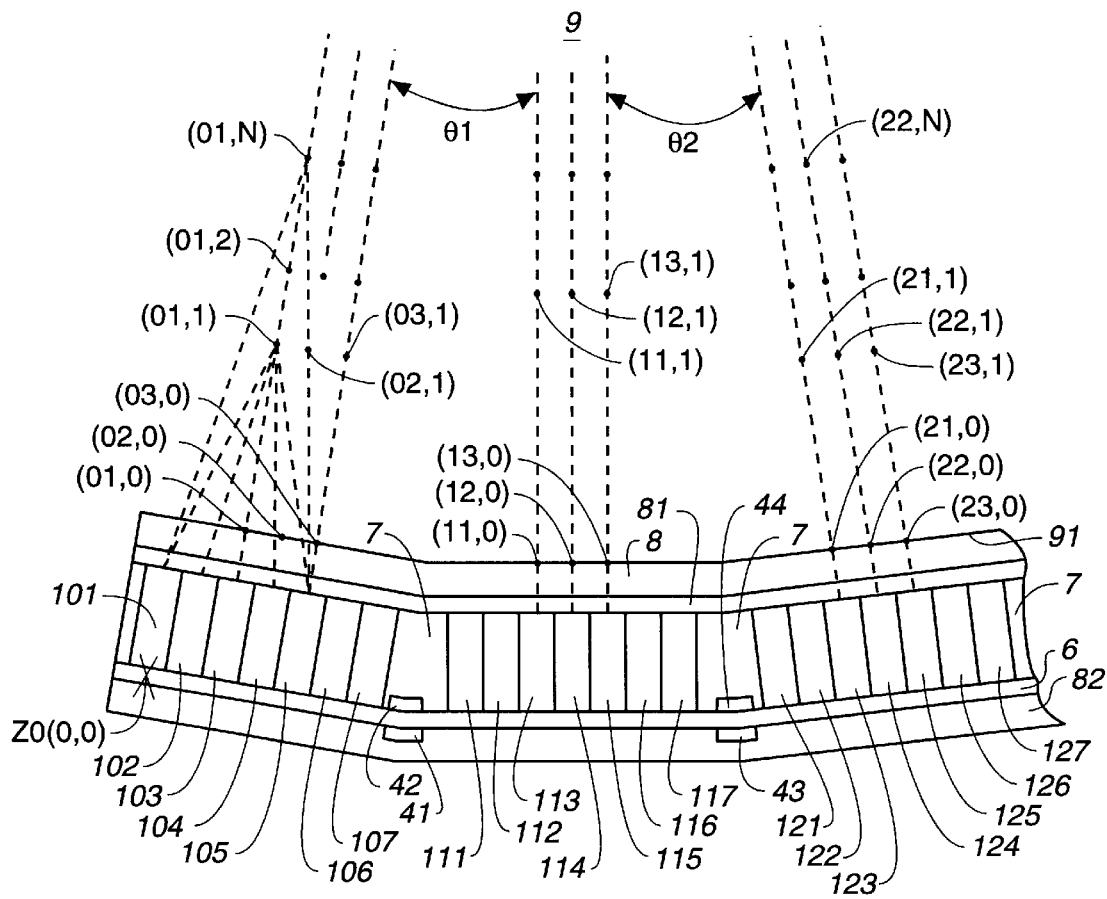
FIG._1
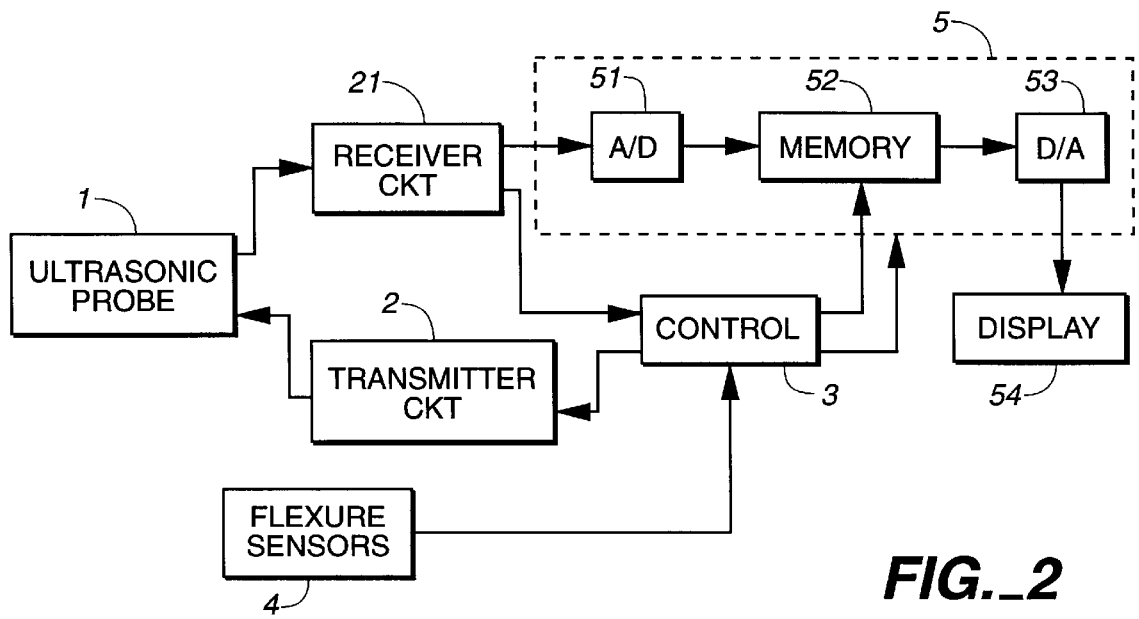
FIG._2

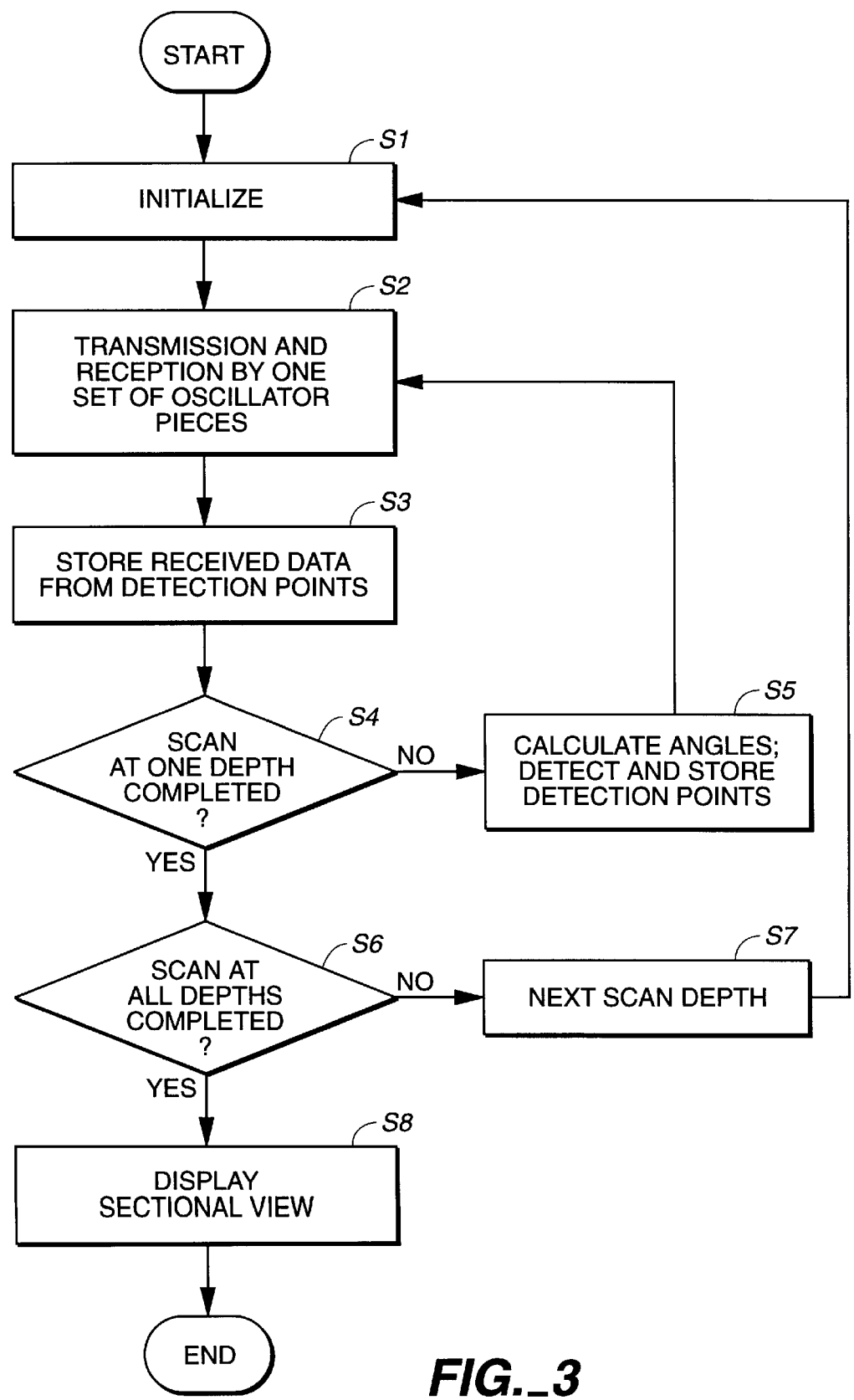
FIG._3

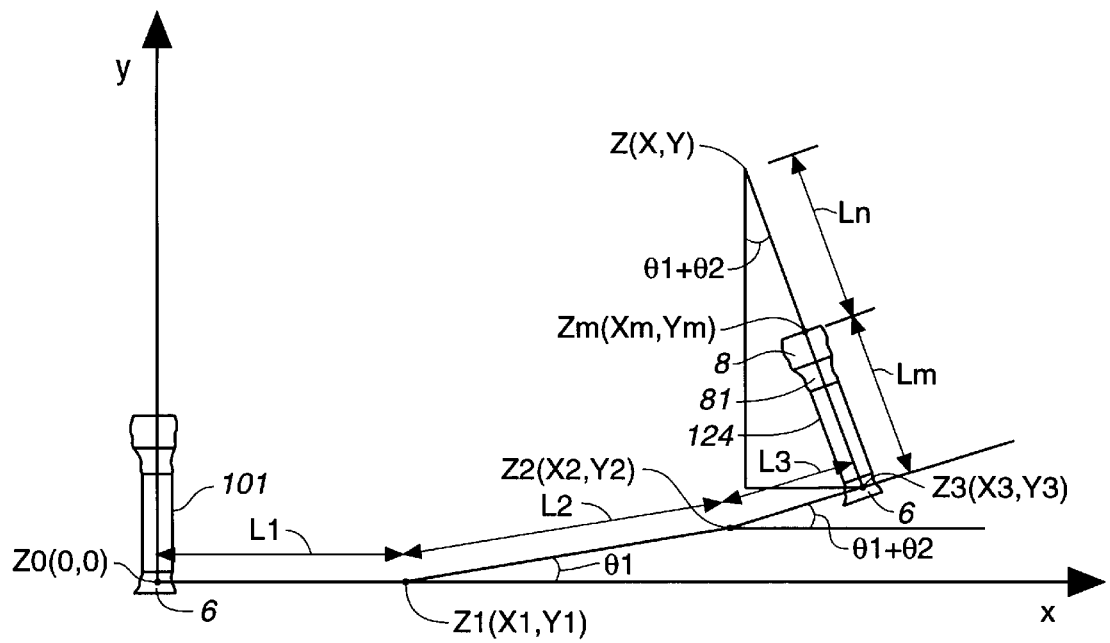
FIG._4
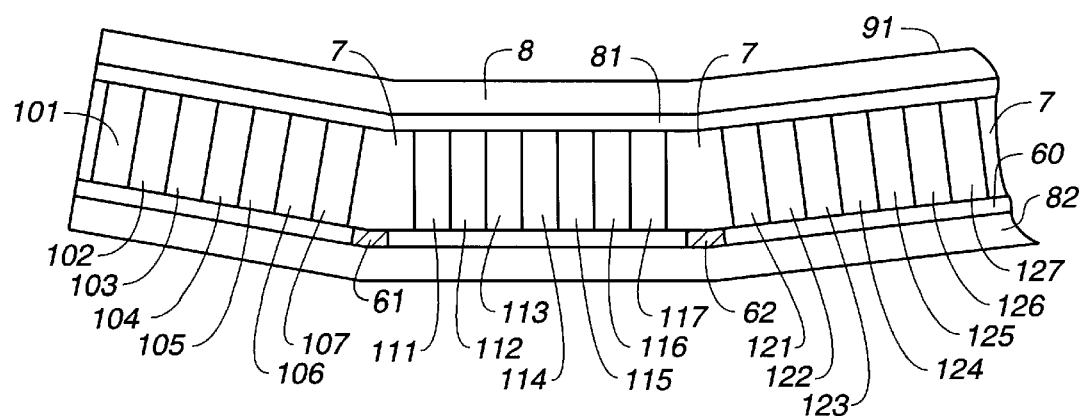
FIG._5

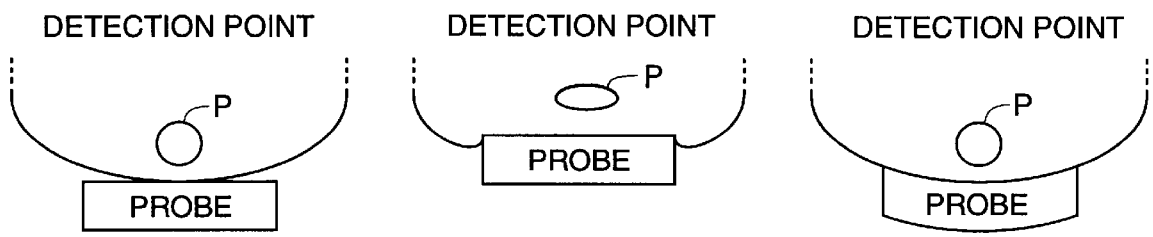
FIG._6A
(PRIOR ART)
FIG._6B
(PRIOR ART)
FIG._6C
(PRIOR ART)
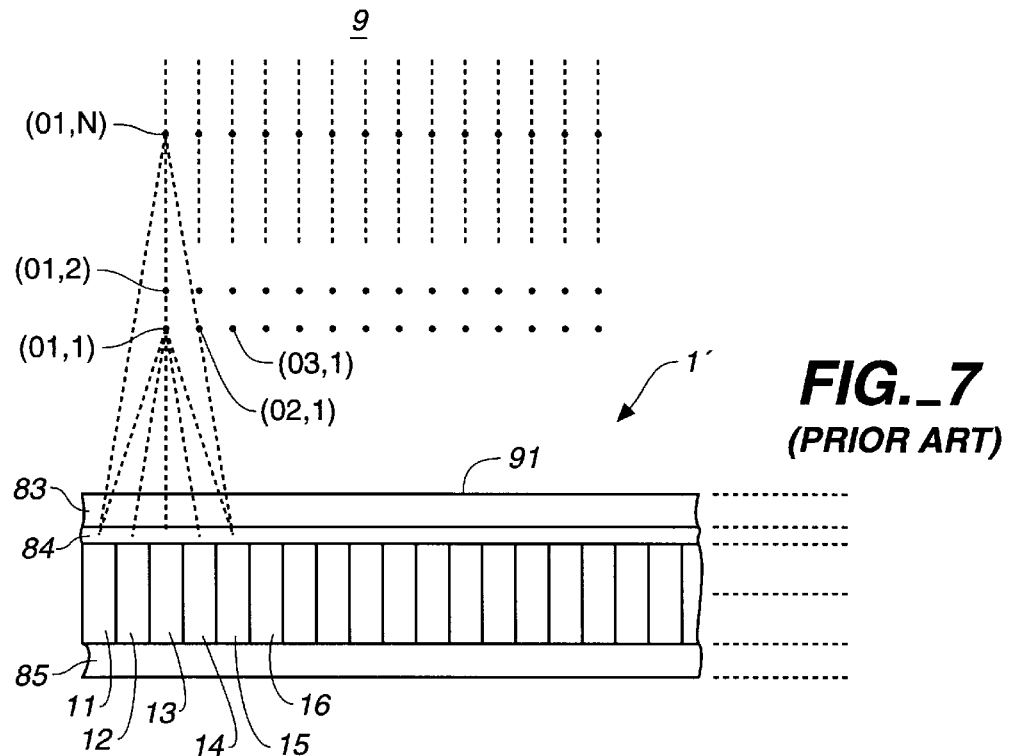
FIG._7
(PRIOR ART)
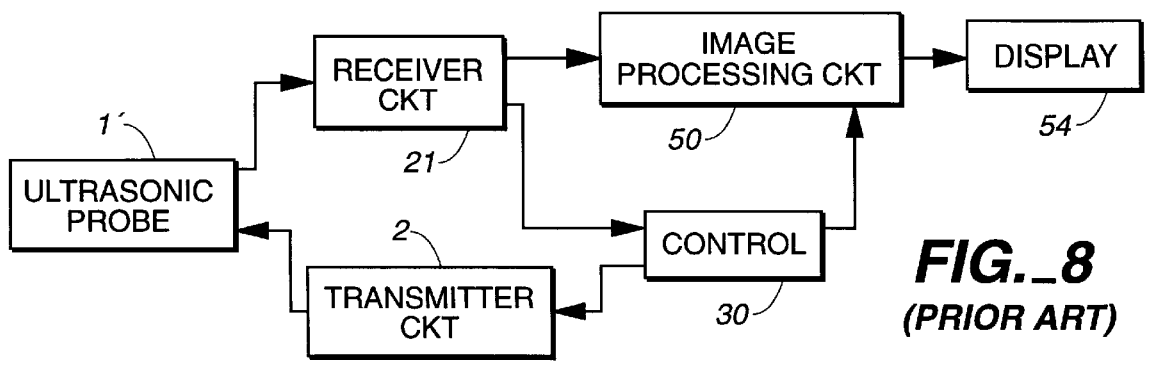
FIG._8
(PRIOR ART)

ULTRASONIC PROBE AND ULTRASONIC SURVEY INSTRUMENT

BACKGROUND OF THE INVENTION

This invention relates to an ultrasonic probe and an ultrasonic scanning instrument capable of bending according to the surface contour of the target body for an ultrasonic visual diagnosis and of thus obtaining an accurate image even from a position close to the body surface.

Although there have been many different kinds of ultrasonic probes for ultrasonic diagnostic apparatus such as a linear type, a convex type and a sector type, the array arrangement of oscillators was always fixed and the direction of ultrasonic wave transmission and reception was also predetermined. FIG. 7 shows a prior art ultrasonic probe 1' comprising a series of oscillator pieces 11, 12, 13, . . . above a sound-absorbing material 85, a matching sheet 84 above the oscillator pieces 11, 12, 13, . . . and below an acoustic lens 83 placed against a surface 91 of a target body 9 to be examined. Detection points inside the target body are indicated by symbols (01, 1), (02, 1), . . . (01, 2), . . . (01, N), . . . . To produce such a probe, a piezoelectric ceramic material is attached to a sound-absorbing material 85, and grooves of a constant measurement are cut by a dicing apparatus to produce oscillator pieces. An array of oscillator pieces is thus produced by repeating the process described above. Ultrasonic waves can be transmitted from these oscillator pieces if a voltage is applied from an ultrasonic transmitter circuit to the electrodes (not shown) attached to these oscillator pieces. Ultrasonic waves thus transmitted into the target body 9 are reflected at a position of detection if there is any reflector at the detection position.

As shown schematically in FIG. 8, a prior art ultrasonic diagnostic apparatus using an ultrasonic probe as shown in FIG. 7 may include, in addition to the ultrasonic probe 1', an ultrasonic wave transmitter circuit 2, a receiver circuit 21, an image processing circuit 50, a display device 54 and a control unit 30 for exciting the oscillator pieces of the probe 1' individually and controlling the transmitter circuit 2 to transmit ultrasonic waves to the target body 9 and the receiver circuit 21 to receive through the oscillator pieces reflected ultrasonic waves from detection positions. The control unit 30 may also be adapted to control the image processing circuit 50 such that ultrasonic diagnostic images are displayed on the display device 54.

Assume, for example, that detection position (01, 1) inside the target body 9 shown in FIG. 7 is of interest. For this purpose, five mutually adjacent oscillator pieces 11–15 may be activated at different times such that ultrasonic waves emitted thereby will reach the detection position at the same time. If there is a reflector at this detection position, the reflected waves will reach these oscillator pieces 11–15 with the same time lags with which the waves were transmitted therefrom. These oscillator pieces are adapted to transmit received waves to the receiver circuit 21, which in turn transmits the received signals to the image processing circuit 50. After this series of operations is completed, the next group of five mutually adjacent oscillator pieces 12–16 is caused to similarly transmit ultrasonic waves to determine whether there is a reflector at the corresponding detection position (02, 1). This operation is further repeated such that detection positions at the same depth (scan depth 1) are scanned continuously until the detection position at the farthest right-hand side (with reference to FIG. 7) is scanned. Thereafter, this series of scanning operations is repeated from the group of oscillator pieces at the left-hand corner of the array to scan detection positions at deeper positions (of scan depth 2). By thus repeating this series of processes at different scan depths, it is possible to display a sectional image, say, of a human organ.

FIG. 6A shows a situation where the prior art ultrasonic probe 1' is only lightly contacted to a curved surface of a target body for visual diagnosis. In this situation, the target body is not deformed by the probe, and the waves emitted from the parts not at the center where the probe and the body are not contacting each other must travel through air before reaching the target body and hence are attenuated. Thus, a correct image of a target P may not be obtained in this situation. If the probe is forcibly pressed against the target body, on the other hand, an extended area of the body surface can be directly in contact with the probe, as shown in FIG. 6B, but a target P near the body surface becomes deformed.

With such a prior art probe, accurate images could not be obtained from body parts with large curvatures such as arms and legs because the probe could not completely contact the body surface. If the probe is pressed too hard onto the body surface, portions of the body near the surface are deformed and cannot provide an accurate sectional view. Worse still, this may be painful to the patient being examined. In summary, prior art probes with a fixed array of oscillators could not provide accurate sectional images of body parts near the surface such as the subcutaneous fat and blood vessels.

It is therefore an object of this invention to provide an ultrasonic probe and an ultrasonic scanning instrument using a flexible base plate which can bend according to the curved body surface as shown in FIG. 6C so as to eliminate the problems of prior art technology described above.

SUMMARY OF THE INVENTION

An ultrasonic probe embodying this invention, with which the above and other objects can be accomplished, may be characterized as having each of its oscillator pieces arranged on a flexible base plate and comprising a flexure detecting sensor disposed at least at one part of this base plate for detecting its degree of flexure. These oscillator pieces maybe divided into sequentially arranged groups, each group having a specified number of the oscillator pieces disposed in a row. The sensors may be flexure detecting elements and may be placed on both sides of the base plate.

An ultrasonic scanning instrument embodying this invention may be characterized not only as comprising an ultrasonic probe as described above, an ultrasonic transmitter circuit for individually exciting the oscillator pieces of the probe, and an image processing circuit for receiving signals received by the oscillator pieces and outputting them as a sectional image on a display device, but also wherein the output from flexure detector sensors on the flexible base plate is displayed on the display device as data which indicate the flexure of the surface of the target body.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic sectional view of a portion of an ultrasonic probe embodying this invention;

FIG. 2 is a block diagram of an ultrasonic scanning instrument using a probe of this invention;

FIG. 3 is a flow chart of an ultrasonic scanning instrument using a flexible probe of this invention;

FIG. 4 is a portion of FIG. 1 for showing positional and orientational relationship of its components;

FIG. 5 is a sectional view of a portion of another ultrasonic probe embodying this invention;

FIGS. 6A, 6B and 6C are sketches of how flexible and non-flexible probes can be pressed against a body surface;

FIG. 7 is a sectional view of a portion of a prior art ultrasonic probe; and

FIG. 8 is a block diagram of a prior art ultrasonic scanning instrument using the probe of FIG. 7.

Throughout herein, the same or substantially equivalent components and objects are indicated by the same numerals for the convenience of description and explanation.

DETAILED DESCRIPTION OF THE INVENTION

FIG. 1 shows a portion of an ultrasonic probe 1 embodying this invention having oscillator pieces 101, 102, . . . , 107, 111, 112, . . . , 117, 121, 122, . . . 127 in groups of seven each, attached in a single row on an elastic metallic plate 6 serving as a flexible base plate. (In practice, there may normally be 12–15 of such groups to constitute a probe.) Each portion of the metallic plate 6 corresponding to one of the groups of seven oscillator pieces is straight. Numerals 7 each indicate a filler material of rubber, numeral 8 indicates an acoustic lens, and numeral 81 indicates a matching sheet, the acoustic lens 8 and the matching sheet 81 being made of a highly expandable rubber material. Numeral 82 indicates a sound-absorbing material, and numerals 9 and 91 again represent a target body and its body surface, respectively. Numerals 41, 42, 43 and 44 indicate resistors (indicated also by numeral 4 when individual ones of them are not distinguished) serving as flexure detecting sensors, attached in pairs on the upper and lower surfaces of the elastic metallic plate 6 between two mutually adjacent groups of the oscillator pieces.

Resistance values of the resistors 41, 42, 43 and 44 change when they are pulled. When the elastic metallic plate 6 is bent upwards as shown in FIG. 1, resistors 41 and 43 change their resistance values. Similarly, resistance values of resistors 42 and 44 change when the elastic metallic plate 6 is bent downward, opposite to FIG. 1. Thus, as will be explained in detail below, changes in the resistance of resistors 41 and 42 can be used to calculate the degree of flexure between the portions of the elastic metallic plate 6 where the group consisting of oscillator pieces 101–107 and the group consisting of oscillator pieces 111–117 are connected. Similarly, changes in the resistance of resistors 43 and 44 can be used to calculate the degree of flexure between the portions of the elastic metallic plate 6 where the group consisting of oscillator pieces 111–117 and the group consisting of oscillator pieces 121–127 are connected.

For the convenience of explanation and description, let Z0 indicate, as shown in FIGS. 1 and 4, the point where the center line of oscillator piece 101 crosses the plane at one-half width of the elastic metallic plate 6, and a two-dimensional x-y coordinate system is set up with Z0 at its origin, the x-axis in the direction of the first straight portion of the metallic plate 6 supporting the first group of the oscillator pieces 101–107 and the y-axis extending along the center line of the oscillator piece 101 towards the target body 9, perpendicularly to the x-direction.

FIG. 2 shows an ultrasonic scanning instrument using the probe 1 according to this invention. For convenience of explanation, components which are equivalent or substantially similar to those shown and explained above with reference to FIG. 8 will be indicated by the same numerals. FIG. 2 shows the ultrasonic scanning instrument as further comprising an ultrasonic wave transmitter circuit 2, an ultrasonic receiver circuit 21, flexure sensors 4, an image processing circuit 5 including an analog-to-digital (A/D) converter 51, an image memory device 52 and a digital-to-analog (D/A) converter 53, a display device 54 and a control unit 3 for causing the oscillator pieces of the probe 1 individually and controlling the transmitter circuit 2 transmitting ultrasonic waves to the target body 9 (shown in FIG. 1) and the receiver circuit 21 receiving reflected ultrasonic waves through the oscillator pieces. The control unit 3 also serves to receive signals outputted from the flexure sensors 4, to calculate therefrom the angles between mutually adjacent pairs of groups of oscillator pieces of the probe 1, and to transmit the results of such calculations to the image processing circuit 5. The control unit 3 further serves to cause the display device 54 to display diagnostic images interpolated according to data received from the flexure sensors 4.

Operations of an ultrasonic scanning instrument thus structured will be explained next with reference to the flow chart of FIG. 3. For the purpose of explanation, let us assume that five mutually adjacent oscillator pieces are caused to transmit ultrasonic waves to each detection position within the target body 9 and the same five oscillator pieces are used to receive the waves reflected at the same detection position. As shown in FIG. 1, furthermore, various points of interest in the following explanation will be indicated each by a set of one two-digit number and one one-digit number such as (pq, r) where r indicates the "scan depth" of the point if r is a non-zero integer, r being 0 if the point is on the upper surface of the acoustic lens 8, and pq indicates that the point is on the center line of the (q+2)nd oscillator piece in the (p+1)st group, where q=1, 2 or 3.

As an initialization step (Step S1), the control unit 3 stores in the memory device 52 the position data of the surface point (01, 0), that is, the point on the upper surface of the acoustic lens 8 on the central axis of the third oscillator piece 103 (which is the middle one of the first five oscillator pieces 101–105 of the first group). This surface point may also be referred to as the body-contacting point because this is where the acoustic lens 8 contacts the body surface 91 of the target body 9. The position data of detection point (01, 1) at scan depth 1 are also stored in the memory device 52. Next, this is repeated for points (02, 0) and (02, 1) which are the point on the surface of the acoustic lens 8 and the detection point at scan depth 1 on the center line of the fourth oscillator piece 104 (which is the middle one of the second five oscillator pieces 102–106 of the same (first) group and then for points (03, 0) and (03, 1) which are respectively the point on the surface of the acoustic lens 8 and the detection point at scan depth 1 on the center line of the fifth oscillator piece 105 (which is the middle one of the third five oscillator pieces 103–107 of the first group). Because the x-axis and the y-axis are defined as above, the x-coordinates and the y-coordinates of these can be easily stored in the initialization step.

Next, controlled by the control unit 3, the ultrasonic wave transmission circuit 2 activates the first five mutually adjacent oscillator pieces 101–105 individually at different times such that the ultrasonic waves emitted from them will reach the detection point (01, 1) on the center line through the middle oscillator piece 103 (of these five pieces 101–105) at scan depth 1 at the same time (Step S2). As reflected waves from this detection point (01, 1) are received, these five oscillator pieces 101–105 output them to the ultrasonic wave receiver circuit 21 where these received signals are amplified before they are transmitted to the image processing circuit 5. In the image processing circuit 5 which is also controlled by the control unit 3, the amplified signals are converted into digital signals by the A/D converter 51 and stored in the image memory device 52 corresponding to the position data for the detection point (01, 1) (Step S3).

Next, the control unit 3 repeats the same operations (NO in Step S4) by activating the next five oscillator pieces 102–106 such that the ultrasonic waves transmitted from them will simultaneously reach the detection point (02, 1) which is on the center line of the middle oscillator piece 104 and at scan depth 1. As reflected waves from the detection point (02, 1) are received by these oscillator pieces 102–106 and transmitted to the ultrasonic wave receiver circuit 21, they are similarly processed and transmitted to the image processing circuit 5 where they are converted into digital data to be stored in the image memory device 52 corresponding to the position data for the detection point (02, 1).

Next, the same operations are repeated with the next five oscillator pieces 103–107 and the digital data corresponding to the detection point (03, 1) on the center line of the middle oscillator piece 105 are stored in the image memory device 52 corresponding to the position data for the detection point (03, 1).

After this series of detection operations is over with the first group of oscillator pieces 101–107 for detection points (01, 1), (02, 1) and (03, 1), the angle θ1, shown in FIG. 4, between the straight portion of the elastic metallic plate 6 supporting the first group of oscillator pieces 101–107 and next straight portion of the elastic metallic plate 6 supporting the second group of oscillator pieces 111–117 is detected by the resistors serving as flexure sensors 4. If the elastic metallic plate 6 is bent upwards, as shown in FIG. 1, for example, the resistor 41 on the lower surface of the metallic plate 6 is pulled from both sides and its resistance value changes. The control unit 3 receives changes in the resistance data to calculate the angle θ1 (Step S5).

Since the position data (x and y coordinates) of the point Z1 where the metallic plate 6 bends between the portion supporting the first group of oscillator pieces 101–107 and the portion supporting the second group of oscillator pieces 111–117 are already known, this detected angle θ1 may be used to obtain the position data of the body-contacting point (11, 0) on the top surface of the metallic plate 6 on the center line of the middle one (113) of the first five oscillator pieces 111–115 of the second group, as well as of the detection point (11, 1) on the same center line and at scan depth 1. These position data are stored in the image memory device 52 (Step S5). Similarly, the body-contacting points (12, 0) and (13, 0) and detection points (12, 1) and (12, 1) at scan depth 1, respectively on the center lines of oscillator pieces 114 and 115 are calculated and stored in the image memory device 52 (Step S5).

As done with the oscillator pieces 101–107 of the first group, as described above, the control unit 3 activates the first five (111–115) of the seven oscillator pieces 111–117 of the second group such that reflected waves from the detection point (11, 1) are received by the same five oscillator pieces 111–115, processed through the ultrasonic wave receiving circuit 21 and the A/D converter and stored in the image memory device 52 corresponding to the position data of the detection point (11, 1) (Steps S2 and S3). Next, the next five oscillator pieces 112–116 are activated, reflected waves from the detection point (12, 1) are received, and data thereon are stored in the image memory device 52 corresponding to the position data of the detection point (12, 1). Lastly, the five oscillator pieces 113–117 are activated, reflected waves from the detection point (13, 1) are received, and data thereon are stored in the image memory device 52 corresponding to the position data of the detection point (13, 1) (Steps S2 and S3).

Next, the control unit 3 calculates the angle θ2, shown in FIG. 4, between the straight portion of the elastic metallic plate 6 supporting the second group of oscillator pieces 111–117 and the next straight portion of the elastic metallic plate 6 supporting the third group of oscillator pieces 121–127 (Step S5). Thereafter, the control unit 3 repeats with the oscillator pieces of the third and subsequent groups what it has done with the oscillator pieces of the first and second groups, thereby scanning all the detection points at scan depth 1 and storing digital data on reflected waves therefrom corresponding to the position data of these detection points (Yes in Step 4 of FIG. 3).

Next, the detection points at scan depth 2 are scanned (No in Step S6 and going on to Step S7). This time, the control unit 3 starts by storing in the image memory device 52 the position data of the detection point (01, 2) on the center line of the oscillator piece 113 at scan depth of 2. Position data of other detection points at scan depth 2, that is, (02, 2), (03, 2), (11, 2), . . . are similarly stored.

Each time, five mutually adjacent oscillator pieces are activated, as explained above, and reflected waves from the corresponding detection point at scan depth 2 are processed similarly (Steps S1, S2 and S3).

When all of the detection points at scan depth 2 are scanned, detection points at scan depth 3 are scanned similarly. This is repeated until detection points at all desired scan depths have been scanned.

FIG. 4 will be referenced next to describe how position data of body-contacting points and detection points can be calculated. For the convenience of explanation, the x-coordinate and the y-coordinate of an exemplary detection point Z on the center line of oscillator piece 124 and at scan depth N will be calculated.

Let L1 be the length of the first straight portion of the metallic plate 6 supporting the first group of oscillator pieces 101–107, that is, the distance between Z0 and the junction point Z1 between the first and second straight portions of the metallic plate 6 respectively supporting the oscillator pieces of the first and the second groups. Similarly, let L2 be the length of the second straight portion of the metallic plate 6 supporting the second group of oscillator pieces 111–117 and Z2 be the junction point between the second and third straight portions of the metallic plate 6. Let Z3 be the point where the center line of the oscillator piece 124 penetrates half-way through the metallic plate 6 and let L3 be the distance between points Z2 and Z3. Let Lm (of a constant value) be the sum of the thickness of the acoustic lens 8, the thickness of the matching sheet 81, the height of each oscillator piece and one-half thickness of the metallic plate 6, and let Ln be the distance between the detection point of interest Z and the corresponding body-contacting point Zm. Then, the x- and y-coordinates of junction point Z1 is are:

$$X1 = L1 \text{ and } Y1 = 0.$$

The x- and y-coordinates of junction point Z2 are:

$$X2 = X1 + L2 \cos\theta 1 = L1 + L2 \cos\theta 1;$$

$Y2 = Y1 + L2 \sin\theta1 = L2 \sin\theta1.$

The x- and y-coordinates of point Z3 are:

$X3 = X2 + L3 \cos(\theta1+\theta2) = L1 + L2 \cos\theta1 + L3 \cos(\theta1+\theta2);$ $Y3 = Y2 + L3 \sin(\theta1+\theta2) = L2 \sin\theta1 + L3 \sin(\theta1+\theta2).$ The x- and y-coordinates of the body-contacting point Zm where the center line of the oscillator piece 124 crosses the surface of the acoustic lens 8 are:

$Xm = X3 - Lm\sin(\theta1 + \theta2)$
$= L1 + L2\cos\theta1 + L3\cos(\theta1 + \theta2) - Lm\sin(\theta1 + \theta2);$
$Ym = Y3 + Lm\cos(\theta1 + \theta2)$
$= L2\sin\theta1 + L3\sin(\theta1 + \theta2) + Lm\cos(\theta1 + \theta2).$ The x- and y-coordinates of the detection point Z at scan depth N are:

$X = X3 - (Ln + Lm)\sin(\theta1 + \theta2)$
$= L1 + L2\cos\theta1 + L3\cos(\theta1 + \theta2) - (Ln + Lm)\sin(\theta1 + \theta2);$
$Y = Y3 + (Ln + Lm)\cos(\theta1 + \theta2)$
$= L2\sin\theta1 + L3\sin(\theta1 + \theta2) + (Ln + Lm)\cos(\theta1 + \theta2).$ The coordinates of the points Z and Zm are related as follows:

$X = Xm - Ln \sin(\theta1+\theta2);$ $Y = Ym + Ln \cos(\theta1+\theta2).$

When detection points at all preliminarily specified scan depths have been scanned (Yes in Step S6 of FIG. 3), the image memory device 52 now stores the position data of all these detection points and the digital data of reflected waves from all these points. The control unit 3 carries out calculations and interpolation for the convenience of a display, inputs the interpolated data in the image memory device 52 and convert them into analog brightness signals by means of the D/A converter 53, causing a sectional view (with the body surface condition taken into account) to be displayed on the display device 54 (Step S8). Display may also be made of numerical data, such as describing the body surface curvature. With an instrument thus structured, it is possible to display the shape of an organ of a human body, like the target P shown in FIG. 6C, with accurate positional relationship. In this example, position data of the body surface contact point and the target point are obtained for each scan at a different depth.

Although the invention has been described above with reference to only one example, this example is not intended to limit the scope of the invention. Many modifications and variations are possible within the scope of this invention. FIG. 5 shows, using the same numerals as in FIG. 1 to indicate identical or equivalent components, a portion of another ultrasonic probe embodying this invention characterized as using flexure detectors in parts 61 and 62 of the elastic metallic plate 6 for detecting the degrees of flexure of the plate 6 between its portions supporting oscillator pieces of different groups.

Although FIG. 1 shows an example wherein seven oscillator pieces form one group, the number of oscillator pieces in each group is not intended to limit the scope of the invention. This number, for example, may be increased to ten. Similarly, although five oscillator pieces are activated according to the example of FIG. 1 to scan each detection point, the number of oscillator pieces to be activated to scan each detection point may be appropriately varied. The angles between straight portions of the metallic plate 6 may be detected by using different kinds of sensors such as optical elements adapted to detect changes in the amount of energy or magnetic elements adapted to detect changes in magnetic flux. Although FIG. 1 relates to a situation wherein the plate 6 is bent upward towards the target body 9, the probe works equally well in situations where the plate 6 is bent so as to be convex towards the target body 9. In such a situation, it will be the resistors 42 and 44 on the lower surface of the plate 6 that will output signals indicative of the flexure.

FIG. 1 shows a situation where the plate 6 bends relatively little such that there is no crossing of detection points associated with oscillator pieces of different groups at any scan depth. If the flexure is large enough to cause such a crossing, a maximum flexure may be preliminarily set or the control unit 3 may be so programmed as to ignore signals from such an overlapping detection points.

There are no stringent limitations on the acoustic lens or the matching sheet. They may be made flexible or stretchable only at positions between oscillator pieces belonging to different groups.

In summary, all such modifications and variations that may be apparent to a person skilled in the art are intended to be within the scope of this invention. In summary, this invention makes it possible to obtain accurate sectional images of even such body parts that are close to the surface or arms and legs where the radius of curvature is small because the detection probe can bend along the body surface.

What is claimed is:

1. An ultrasonic probe comprising:

a flexible base plate;

a plurality of oscillator pieces each for transmitting and receiving ultrasonic waves, said plurality of oscillator pieces being divided into sequentially arranged groups, each group having a specified number of said oscillator pieces disposed in a row on said base plate, wherein each of portions of said base plate supporting a corresponding one of said groups of oscillator pieces is straight; and sensors attached to said base plate between mutually adjacent pairs of said groups for detecting degrees of flexure of said base plate, said sensors being adapted to detect angles between mutually adjacent pairs of said portions of said base plate.

2. An ultrasonic scanning instrument comprising:

a probe having a plurality of oscillator pieces aligned on a flexible base plate and each adapted to transmit and receive ultrasonic waves and sensors attached to said base plate for detecting degrees of flexure of said base plate;

a transmission circuit for individually causing said oscillator pieces to transmit ultrasonic waves;

a display device for displaying data;

an image processing device for receiving ultrasonic wave signals through said oscillator pieces and signals from said sensors and causing said display device to display a sectional view of a target object with a curved surface contacting said base plate.

3. The ultrasonic scanning instrument of claim 2 wherein said plurality of oscillator pieces are divided into sequentially arranged groups, each group having a specified number of said oscillator pieces disposed in a row on said base plate, said sensors being attached between mutually adjacent pairs of said groups.

4. The ultrasonic scanning instrument of claim 3 wherein each of portions of said base plate supporting a corresponding one of said groups of oscillator pieces is straight, wherein said sensors are adapted to detect angles between mutually adjacent pairs of said portions of said base plate, and wherein said angles are incorporated in displaying said sectional view on said display device.

5. The ultrasonic scanning instrument of claim 2 wherein said plurality of oscillator pieces are divided into sequentially arranged groups, each group having a specified number of said oscillator pieces disposed in a row on said base plate, said sensors being attached between mutually adjacent pairs of said groups.

6. The ultrasonic scanning instrument of claim 5 wherein each of portions of said base plate supporting a corresponding one of said groups of oscillator pieces is straight, wherein said sensors are adapted to detect angles between mutually adjacent pairs of said portions of said base plate, and wherein said angles are incorporated in displaying said sectional view on said display device.

7. An ultrasonic probe comprising:

a flexible base plate;

a plurality of oscillator pieces each for transmitting and receiving ultrasonic waves, said oscillator pieces being aligned on said base plate and controlled to transmit ultrasonic waves at individually different times; and sensors attached to said base plate for detecting degrees of flexure of said base plate.

8. The ultrasonic scanning instrument of claim 2 wherein said transmission circuit causes said oscillator pieces to transmit ultrasonic waves at different times, depending at least in part on said degrees of flexure of said base plate detected by said sensors.

9. The ultrasonic scanning instrument of claim 2 wherein said transmission circuit causes said oscillator pieces to transmit ultrasonic waves at different times, depending at least in part on said degrees of flexure of said base plate detected by said sensors.

10. The ultrasonic scanning instrument of claim 2 wherein said transmission circuit causes said oscillator pieces to transmit ultrasonic waves at different times, depending on said degrees of flexure of said base plate detected by said sensors and the position of said target object.

11. The ultrasonic scanning instrument of claim 2 wherein said transmission circuit causes said oscillator pieces to transmit ultrasonic waves at different times, depending on said degrees of flexure of said base plate detected by said sensors and the position of said target object.

* * * * *